US011471560B2

(12) United States Patent
Williams et al.

(10) Patent No.: US 11,471,560 B2
(45) Date of Patent: *Oct. 18, 2022

(54) CANCELLOUS BONE PRODUCT INCLUDING VIABLE OSTEOGENIC CELLS

(71) Applicant: NuVasive, Inc., San Diego, CA (US)

(72) Inventors: Michelle Leroux Williams, Laurel, MD (US); Charles Randal Mills, Finksburg, MD (US); Rodney Monroy, Aberdeen, MD (US)

(73) Assignee: NuVasive, Inc., San Diego, CA (US)

( * ) Notice: Subject to any disclaimer, the term of this patent is extended or adjusted under 35 U.S.C. 154(b) by 337 days.

This patent is subject to a terminal disclaimer.

(21) Appl. No.: 16/685,942

(22) Filed: Nov. 15, 2019

(65) Prior Publication Data

US 2020/0101196 A1    Apr. 2, 2020

Related U.S. Application Data

(63) Continuation of application No. 15/596,237, filed on May 16, 2017, now Pat. No. 10,507,265, which is a continuation of application No. 13/915,569, filed on Jun. 11, 2013, now abandoned, which is a continuation of application No. 11/799,606, filed on May 2, 2007, now Pat. No. 8,460,860.

(60) Provisional application No. 60/831,723, filed on Jul. 18, 2006, provisional application No. 60/798,474, filed on May 8, 2006.

(51) Int. Cl.
| | |
|---|---|
| *A61L 27/36* | (2006.01) |
| *C12N 5/077* | (2010.01) |
| *A61L 27/54* | (2006.01) |
| *A61F 2/28* | (2006.01) |

(52) U.S. Cl.
CPC ......... *A61L 27/3608* (2013.01); *A61L 27/365* (2013.01); *A61L 27/3683* (2013.01); *A61L 27/3687* (2013.01); *A61L 27/54* (2013.01); *C12N 5/0654* (2013.01); *A61F 2/28* (2013.01); *A61F 2310/00359* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 5,118,512 A | 6/1992 | O'Leary et al. | |
| 5,788,941 A | 8/1998 | Dalmasso et al. | |
| 5,901,315 A | 5/1999 | Edwards | |
| 6,203,755 B1 | 3/2001 | Odland | |
| 6,294,187 B1 | 9/2001 | Boyce et al. | |
| 6,652,872 B2 | 11/2003 | Nevo et al. | |
| 6,739,112 B1 | 5/2004 | Marino | |
| 8,460,860 B2* | 6/2013 | Williams | A61L 27/365 435/1.3 |
| 8,834,928 B1* | 9/2014 | Truncale | C12N 5/0654 435/1.3 |
| 8,883,210 B1* | 11/2014 | Truncale | A61K 38/1825 435/1.3 |
| 9,352,003 B1* | 5/2016 | Semler | A61L 27/3847 |
| 10,130,736 B1* | 11/2018 | Semler | A61L 27/3691 |
| 10,507,265 B2* | 12/2019 | Williams | A61L 27/3687 |
| 10,898,611 B2* | 1/2021 | Williams | A61L 27/3608 |
| 2021/0128784 A1 | 5/2021 | Williams et al. | |

FOREIGN PATENT DOCUMENTS

| | | |
|---|---|---|
| WO | 2007133451 A1 | 11/2007 |
| WO | 2009134815 A1 | 11/2009 |

OTHER PUBLICATIONS

Oh et al, Cryobiology, 2002, 44:279-287. (Year: 2002).*
Van der Donk et al, Clin Orthop Rel Res, 2003, 408: 302-310. (Year: 2003).*
U.S. Appl. No. 17/125,837, Applicant NuVasive, filed Dec. 17, 2020. (Year: 2020).*

* cited by examiner

*Primary Examiner* — Allison M Fox
(74) *Attorney, Agent, or Firm* — Hoffman Warnick LLC

(57) ABSTRACT

A bone implant comprising cancellous bone that is essentially free of blood cells, and which has been treated with at least a loosening agent, such as collagenase and/or a digestive enzyme, for a time and at a concentration to loosen the osteogenic cells in the cancellous bone matrix. The osteogenic cells in the matrix are viable cells. The treatment of the cancellous bone with at least one loosening agent enables the osteogenic cells to be more available for carrying out their osteogenic function and to provide for an increased rate of bone formation.

19 Claims, No Drawings

CANCELLOUS BONE PRODUCT INCLUDING VIABLE OSTEOGENIC CELLS

CROSS REFERENCE TO RELATED APPLICATIONS

This application is a continuation application of U.S. patent application Ser. No. 15/596,237, filed in May 26, 2017, which is a continuation application of U.S. patent application Ser. No. 13/915,569 filed on Jun. 11, 2013, which in turn claimed the benefit of, and priority to, U.S. patent application Ser. No. 11/799,606, now U.S. Pat. No. 8,460,860, filed May 2, 2007, which in turn claimed priority to, and the benefit of, U.S. provisional patent application Ser. Nos. 60/831,723, filed Jul. 18, 2006, and 60/798,474, filed May 8, 2006, the contents of which are incorporated herein by reference in their entireties.

BACKGROUND

This invention relates to bone implants which include cancellous bone. More particularly, this invention relates to bone implants that include cancellous bone that has been treated with at least one loosening agent, such as collagenase and/or a digestive enzyme, in order to loosen osteogenic cells in the bone matrix. The cancellous bone also is essentially free of blood cells.

Bone implants which include cancellous bone have been used in a variety of procedures and treatments, including bone fusions such as spine fusions, disc augmentations in the spine, and bone fill applications employed in the treatments of diseases, disorders, or injuries including, but not limited to, avascular osteonecrosis, osteosarcoma, acute fractures and fracture non-unions, as well as for bone regeneration for orthopedic implants. Such bone in general may be harvested from any source of cancellous bone, including vertebrae, the iliac crest, femur, tibia, or ribs.

Cancellous bone implants in general have included, in addition to osteocytes and osteogenic cells, blood cells including hematopoietic cells. In some implants, the implants have been treated in order to preserve the viability of all the cells in the implant, while in other implants, the viability of the bone cells, including the osteogenic cells, has been destroyed.

DETAILED DESCRIPTION

The present invention provides a bone implant which includes cancellous bone including viable osteogenic cells which are made more available for carrying out their osteogenic function.

In accordance with an aspect of the present invention, there is provided a bone implant comprising cancellous bone. The cancellous bone is essentially free of blood cells, and has been treated with at least one loosening agent for a time and at a concentration to loosen the osteogenic cells in the cancellous bone matrix. The osteogenic cells in the bone matrix are viable cells.

The term "loosening agent," as used herein, means an agent which loosens the osteogenic cells in the cancellous bone matrix, but does not release the osteogenic cells from the cancellous bone matrix.

Loosening agents which may be employed include, but are not limited to, collagenase, and digestive enzymes, including, but not limited to, trypsin, amylase, and lipase, or combinations thereof.

In one embodiment, the at least one loosening agent is collagenase. In another embodiment, the at least one loosening agent is a digestive enzyme. In one embodiment, the digestive enzyme is trypsin.

The term "osteogenic cell," as used herein, means any type of cell having osteoprogenitor potential, that is, any type of cell that is capable of differentiating into a bone cell.

Although the scope of the present invention is not to be limited to any theoretical reasoning, when the bone implant is essentially free of blood cells and has been treated with a loosening agent, such as collagenase and/or a digestive enzyme, in order to loosen the osteogenic cells in the cancellous bone matrix, such osteogenic cells become more available for or are more disposed toward carrying out their osteogenic function, and provide for an increased rate of bone formation. Thus, such bone implants are capable of generating or "growing" bone directly and provide for improved implants vis-a-vis prior art implants, including previously produced cancellous bone implants, and ceramic implants.

The cancellous bone is treated with the loosening agent, such as collagenase and/or a digestive enzyme, for a time and at a concentration to loosen the osteogenic cells in the cancellous bone matrix. In one embodiment, the cancellous bone is treated with the loosening agent, such as collagenase and/or a digestive enzyme, at a concentration of from about 0.1 mg/ml to about 3.0 mg/ml, and in another embodiment from about 1.0 mg/ml to about 3.0 mg/ml. The cancellous bone is treated with the loosening agent, such as collagenase and/or a digestive enzyme, for a period of time to loosen the osteogenic cells in the cancellous bone matrix, but not release the osteogenic cells from the cancellous bone matrix. In one embodiment, the cancellous bone is treated with the loosening agent, such as collagenase and/or a digestive enzyme, for a period of time of from about 5 min. to about 3 hrs., and in another embodiment from about 5 min. to about 30 min. In yet another embodiment, the cancellous bone is treated with the loosening agent, such as collagenase and/or a digestive enzyme, at a concentration of 1.0 mg/ml for 10 minutes.

Although applicants do not intend to be limited to any theoretical reasoning, it is believed that, by treating the bone with the loosening agent, such as collagenase and/or a digestive enzyme, as hereinabove described, such treatment provides for a partial, but not complete, digestion of the components of the bone matrix (such as collagen, for example). Such partial digestion of the components of the bone matrix, loosens, but does not release, osteogenic cells from the matrix, thereby making such cells, as noted hereinabove, more available for or more disposed toward carrying out their osteogenic function.

In general, the cancellous bone is harvested from any cancellous bone bearing source. Such sources include, but are not limited to, vertebral bodies in the spine, the iliac crest, femur, tibia, and ribs. The cortical shell of the bone is removed, and then the bone is cut or milled into desired pieces or shapes. For example, the bone may be cut and/or milled into bone chips, or may be cut into wedges or plugs, or may be formed into pellets.

The bone then is washed to remove blood cells, such as red blood cells and hematopoietic cells. After the bone is washed, the bone is treated with a loosening agent, such as collagenase and/or a digestive enzyme. As noted hereinabove, the bone is treated with the loosening agent, such as collagenase and/or a digestive enzyme, for a time and at a concentration to loosen the osteogenic cells contained in the bone matrix, but not release the osteogenic cells from the bone matrix. In one embodiment, the bone is treated with the loosening agent, such as collagenase and/or a digestive enzyme, at a concentration of from about 0.1 mg/ml to about 3.0 mg/ml, and in another embodiment from about 1.0 mg/ml to about 3.0 mg/ml. The bone is treated for a period of time of from about 5 min. to about 3 hrs., and in another embodiment from about 5 min. to about 30 min. In yet another embodiment, the bone is treated with the loosening agent, such as collagenase and/or a digestive enzyme, at a concentration of 1.0 mg/ml for 10 minutes.

Subsequent to the treatment with the loosening agent, such as collagenase and/or a digestive enzyme, the bone is treated with one or more antibiotics and/or one or more antimycotics in order to reduce the level of bioburden within the bone. Antibiotics which may be employed include, but are not limited to, gentamicin; vancomycin; penicillins; macrolide antibiotics, such as erythromycin; sulfa-based antibiotics, and combinations thereof. Antimycotics which may be employed include, but are not limited to, amphotericin, fluconazole, and combinations thereof.

After the antibiotic and/or antimycotic treatment, when chipped or milled bone is employed, the chipped or milled bone, if desired, may be filtered through sieves in order to retain pieces of the bone which have a desired size.

After the bone has been washed, treated with the loosening agent, such as collagenase and/or a digestive enzyme, and treated with antibiotic and/or antimycotic, the bone then may be added to an appropriate preservation medium, such as a cryopreservation or vitrification medium, in which the bone may be preserved and stored, and the osteogenic cells contained therein will remain viable. In one embodiment, the preservation medium may include glycerol and/or dimethylsulfoxide, or DMSO. In one embodiment, the preservation medium enables the treated bone to be frozen at temperatures as low as −140.degree. C. and as high as −20.degree. C. while maintaining the viability of the osteogenic cells. It is also contemplated within the scope of the present invention that the cancellous bone treated with a loosening agent, such as collagenase and/or a digestive enzyme, may be combined with bone that has not been treated with a loosening agent prior to packaging as a final product. For example, the cancellous bone treated with the loosening agent may be mixed with bone that has not been treated with a loosening agent, such as allograft bone chips, fragments or powder, or nucleus pulposus. For example, in one embodiment, the bone treated with the loosening agent may be admixed with demineralized bone prior to formulation into a final product. In another embodiment, the final product includes 50 vol. % treated bone, and 50 vol. % untreated bone.

The bone implant treated with the loosening agent may be administered to an animal in an amount effective to treat a bone disease, disorder, defect, or injury in the animal. The animal may be a mammal, including human and non-human primates. In one embodiment, the animal is a human.

Bone diseases, disorders, defects, or injuries which may be treated by the bone implant treated with the loosening agent include, but are not limited to, degenerative disc disease, avascular osteonecrosis, osteosarcoma fractures, and fracture non-unions. The bone implant treated with the loosening agent also may be employed in bone fusions, such as spine fusions, as well as in disc augmentation, and for bone regeneration in orthopedic implants.

The bone implant treated with the loosening agent may be administered directly to the site of the bone disease, disorder, defect, or injury. Depending upon the form and/or shape of the implant, the implant may be injected directly into the site affected by the bone disease, disorder, defect, or injury, or the implant may be packed directly into the site affected by the bone disease, disorder, defect, or injury. The implant has a sufficient consistency such that the implant will be retained at the implantation site long enough for initial bone formation, osteoinductive signaling, and host cell attachment to occur. It is also contemplated within the scope of the present invention that the bone implant may be employed in conjunction with devices employed in the treatment of bone diseases, defects, disorders, and injuries, such as, for example, orthopedic cage devices, ceramics, or plates which may be employed in the spine or in bones to promote bone growth and fusion. Furthermore, the bone implant may be used in conjunction with an autologous bone graft. The bone implant also may be administered with antibiotics, such as those hereinabove described, antimycotics, or anti-inflammatory agents. In another embodiment, the bone implant may be administered in combination with osteoinductive factors such as, for example, bone morphogenic proteins, or BMPs, such as BMP-2 and BMP-7, and platelet-derived growth factor (PDGF), which enhance the osteogenic potential of the bone implant. It is to be understood, however, that the scope of the present invention is not intended to be limited to the treatment of any particular bone disease, defect, disorder, or injury, or to any particular fault or any particular method of administration of the bone implant.

The invention now will be described with respect to the following examples. It is to be understood, however, that the scope of the present invention is not intended to be limited thereby.

EXAMPLE 1

A bone sample was removed from a saline holding solution after debridement of soft tissue, and swabbed with a wiper. The bone was placed in a cutting area, and positioned face up. The bone then was cut with a reciprocating saw to remove the cortical shell. The remaining bone then was placed into a 500 ml washing bag filled halfway with saline (0.9%) and anticoagulant citrate dextrose solution, Formula A (ACD-A), at a ratio of 9 parts 0.9% saline to one part ACD-A. The bag lid then was closed, and shaken vigorously. The bone sample then was retrieved from the washing solution, and then placed into a bone milling chamber. The bone was then milled, and then the milled bone was spooned out, and placed into a 500 ml receiver bottle containing up to 300 ml of 0.9% saline and ACD-A at a volume ratio of 9 parts saline to one part ACD-A.

The milled bone then was washed. First, the wash solution was decanted from the receiving bottle into a waste beaker. The wash solution was replaced with a new wash solution of 0.9% saline and ACD-A (volume ratio of 9 parts saline to one part ACD-A), the lid on the receiver bottle was tightened, and the bottle was shaken vigorously. The above washing was repeated until the wash solution was clear, and the chips of milled bone were white to off-white in color. The last wash solution was decanted, and the bone chips were removed from the receiver bottle with a sampler spoon. Using a Petri dish and forceps, bone samples then were separated out from large blood clot pieces and tissues. The bone then was packed into a 50 ml conical tube, and the total volume was recorded. The total volume of bone chips was split by separating half for collagenase treatment and half for fresh chips. The chips designated for collagenase treatment were placed into a sterile 500 ml receiver bottle, and the fresh chips were placed into a 500 ml receiver bottle and covered with 0.9% saline and ACD-A at a volume ratio of 9 parts saline to one part ACD-A.

A collagenase solution then was prepared by mixing a collagenase powder with PBS in an amount of 1 mg collagenase for each milliliter of PBS. The collagenase solution was added to the milled bone designated for the collagenase treatment in an amount of 2 ml collagenase solution for each cc of bone to be treated. The bottle containing the milled bone and the collagenase solution then was placed, with the lid loose, onto a rocker inside a 37.degree. C. incubator for 10 minutes.+-.1 minute. The bottle then was removed from the incubator, and the collagenase solution was decanted into a bottle(s). The collagenase treated milled bone then was rinsed by adding the same volume of PBS and ACD-A at a volume ratio of 9 parts PBS to one part ACD-A. This rinsing solution then was decanted into the bottle containing the collagenase solution. The rinsing then was repeated, the rinsing solution again was decanted, and the collagenased bone sample was added to the bottle of fresh bone sample. The resulting combined (collagenase treated plus fresh) bone sample then was poured through a 1 mm sieve and placed in a clean bottle. The combined bone sample then was rinsed with Dulbecco's Minimal Essential Medium (DMEM), low glucose, with phenol, prior to antibiotic treatment. A demineralized bone sample also was rinsed with DMEM prior to antibiotic treatment.

A 1.times. antibiotic solution then was prepared. For each 1 ml of solution, 0.9 ml of DMEM was mixed with 0.005 ml of 10 mg/ml gentamicin sulfate, 0.05 ml of 50 mg/ml vancomycin HCl, and 0.01 ml of 250 .mu.g/ml amphotericin B. Thus, the antibiotic solution included gentamicin sulfate at a concentration of 50 .mu.g/ml, vancomycin HCl at a concentration of 50 .mu.g/ml, and amphotericin B at a concentration of 2.5 .mu.g/ml.

The antibiotic solution then was added to each of the combined bone sample and the demineralized bone sample in an amount of 2 ml for each 1 cc of bone sample. The bottles then were placed onto a rocker inside of a 37.degree. C. incubator, with the lids loose, for no less than 18 hours. The bottles then were removed from the incubator, placed under a biological safety container, and the antibiotic solutions were decanted from each of the combined bone sample, and the demineralized bone sample, and each of the bone samples then was washed with the same volume of PBS. The samples then were shaken vigorously. The rinse solutions from the PBS wash were retained, and the pH of each solution was determined. The samples were washed with PBS until the pH of the rinse solutions was in the range of 5.0 to 7.5. After the PBS washing was completed, PBS was decanted from each of the bone samples, and the same volume of Plasma Lyte-A (Baxter) solution, which includes 140 meq/l Na.sup.+, 5 meq/l K+, 98 meq Cl-, 3 meq Mg.sup.2+, and 27 meq/l acetate, was added to each bone sample. The bone samples were shaken vigorously, and the Plasma Lyte-A washing was repeated twice for each sample.

Using a sampler spoon, a 50 ml conical tube was packed gently with the combined (collagenased and fresh) bone sample, and a demineralized bone sample was packed gently into a 15 ml conical tube. 5 ml of a cryopreservation solution was added to the 15 ml conical tube and shaken vigorously. Each ml of cryopreservation solution included 0.7 ml of 1.times. Plasma Lyte-A, 0.2 ml of 25% human serum albumin, and 0.1 ml of 1.times. dimethylsulfoxide (DMSO) (CryoServ.) The final concentration of human serum albumin, therefore, was 5% and the final concentration of dimethylsulfoxide was 10%. After shaking, the demineralized bone sample was transferred to the 50 ml conical tube holding the cancellous bone, and then 10 ml of cryopreservation solution were added to the 50 ml conical tube and shaken vigorously. The entire sample then was placed in a product dose jar. 5 ml of cryopreservation solution then were added to the product dose jar. If the bone product were not covered with solution, up to 5 ml more of cryopreservation solution were added. The jar then was sealed. After the jar was sealed, the product dose jar was placed into a packaging bag. The bag then was sealed. The secondary packaging bag and a package insert then were placed into a tertiary mailer package, which then was heat sealed. The mailer package then was placed into an -80.degree. C. quarantine freezer until the bone product was ready to be used.

EXAMPLE 2

A bone product from a single donor was prepared as described in Example 1, except that, instead of storing 50 ml samples at -80.degree. C., fourteen 5 cc doses were labeled and stored at -50.degree.C.+-.5.degree.C. and six 5 cc doses were labeled and stored at -80.degree.C.+-.5.degree.C. Seventeen days after freezing, three of the doses stored at -50.degree.C. and three of the doses stored at -80.degree.C. were thawed.

The jars containing the frozen bone samples placed in a 37.degree.C. water bath until the entire frozen products were thawed. The jars were removed from the water bath immediately upon thawing, and sprayed with 70% isopropanol. The outsides of the jars then were dried. The jars then were transferred to a biological safety cabinet, the lids were removed, and the thawed cryopreservation solutions were aspirated directly from the jars. 25 ml of Dulbecco's Minimal Essential Medium-low glucose (DMEM-lg) then were added to each of the jars, and the containers were swirled such that the DMEM-lg covered the entire bone samples completely. The DMEM-lg then was aspirated from each jar, and the entire bone samples were transferred to 50 ml conical tubes. An additional 25 ml of DMEM-lg then were added to each of the conical tubes containing the bone samples.

A 1 mg/ml collagenase solution (1 mg/1 ml PBS) was prepared in a 250 ml receiver bottle. 2 ml of collagenase solution were prepared per 1 cc of bone sample.

The DMEM-lg was aspirated from the 50 ml conical tubes containing the bone samples, and then 25 ml of PBS were added to each of the conical tubes, and the tubes were swirled to wash away any remaining DMEM-lg. The washing with PBS was repeated as necessary to remove any DMEM-lg still visible in the bone samples.

After the final PBS wash, the PBS was aspirated off and the bone samples were transferred to 250 ml receiver bottles containing the collagenase solutions. The bottles then were placed onto a rocker inside a 37.degree.C. incubator for 15 minutes.+-.1 minute. The bottles then were removed from the incubator, and the collagenase solutions were pipetted over 70 .mu.m cell strainers into 250 ml conical tubes. The collagenased bone samples then were rinsed with PBS at volumes equal to the original collagenase treatments. The PBS rinses were pipetted over the 70 .mu.m cell strainers into the 250 ml conical tubes. The PBS rinsing was repeated twice, and the conical tubes were placed in a centrifuge (Beckman #GS-6R) and spun at 1960 rpm for 8 minutes (at approximately 878 g). The conical tubes then were transferred to the biological safety cabinet, and the supernatants were aspirated. The pellets then were loosened gently by dragging the tubes across the tube racks. The pellets then were resuspended in appropriate volumes (1 to 4 ml) of PBS/ACD-A (containing 59 ml ACD-A per 500 ml PBS).

Three of the samples that were frozen at −50.degree.C. and three of the samples that were frozen at −80.degree.C. then were tested for cell viability.

Using a 2-20 .mu.l Pipetman pipette (Gilson, No. P20), 20 .mu.l aliquots of the resulting cell suspensions were added to a microcentrifuge tube. 20 .mu.l aliquots of 0.4% Trypan Blue then were added to each of the microcentrifuge tubes, and the contents were mixed by finger tapping. 10 .mu.l of the cell suspensions then were transferred into each side of hemacytometers (Hausser Scientific, Model No. Steri-Cult 200) with a cover slip in place. The cells then were allowed to settle in the counting chambers before starting counts of viable and non-viable cells. The cells were not exposed to the Trypan Blue for more than 10 minutes, to prevent viable cells from absorbing the dye.

With the 10.times. objective of the microscope, the grid lines on each of the chambers' center 1 mm.times.1 mm squares were focused. The slides were positioned such that the central areas of the grids were seen. The objective of the microscope then was changed to the 20.times. objective. The microscope then was focused, and viable and non-viable cells were counted. Viable and non-viable cells in two chambers for each cell suspension were counted. Viable and non-viable cell counts then were determined, from which were calculated the concentration of viable cells, the concentration of all cells, and the % viability of the cells.

In order to be acceptable for in vivo administration, the samples must have a viability of at least 70%, and have a cell density of at least 1.times.10.sup.3 cells/cc.

The viability results for each of the samples are given in Table 1 below.

TABLE 1

| Storage temperature | % Viability | Cells/cc |
|---|---|---|
| 50 ± 5° C. | 78.6 | $8.80 \times 10^5$ |
| 50 ± 5° C. | 77.8 | $7.00 \times 10^5$ |
| 50 ± 5° C. | 79.3 | $5.84 \times 10^5$ |
| 80 ± 5° C. | 76.1 | $5.60 \times 10^5$ |
| 80 ± 5° C. | 77.0 | $5.36 \times 10^5$ |
| 80 ± 5° C. | 81.1 | $6.16 \times 10^5$ |

The above data shows that acceptable viability data were obtained for each sample tested, and that cancellous bone prepared in accordance with the present invention can be stored at −80.degree.C.+−.5.degree.C. at least for seventeen days.

With respect to some applications, surgeons may need to store the cancellous bone at temperature higher than −80.degree.C., such as −50.degree.C. The above data shows that the cancellous bone may be stored at −50.degree.C. and still retain acceptable viability.

EXAMPLE 3

23 samples of collagenase-treated bone were prepared as described in Example 1, except that the bone samples were treated with collagenase at concentrations from 0.167 mg/ml to 3 mg/ml as given in Table 2 below, and for a period of time from 5 min. to 24 hrs., also given in Table 2 below, and the bone samples were not frozen. The volume of each bone sample and the total volume of collagenase used to treat each bone sample also are given in Table 2 below.

The fresh bone samples were tested for % viability and cell density as described in Example 2. The results are given in Table 2 below.

TABLE 2

| Sample | Donor | Carrier for Collagenase | Conc. | Duration | Volume of Bone (cc) | Volume of Collagenase (ml) | Viability | Cell Yield | Cells/cc Bone |
|---|---|---|---|---|---|---|---|---|---|
| 1 | 020505 | DMEM | 0.5 mg/ml | 24 hrs | 18 | 50 | 91.0% | 6.12E+06 | 3.40E+05 |
| 2 | 020805 | DMEM | 0.5 mg/ml | 24 hrs | 12.5 | 30 | 83.5% | 1.68E+05 | 1.34E+04 |
| 3 | 121404 | DMEM | 0.5 mg/ml | 3 hrs | 5 | 30 | 84.0% | 4.80E+05 | 9.60E+04 |
| 4 | 121404 | DMEM | 1.5 mg/ml | 3 hrs | 10 | 30 | 81.0% | 4.40E+06 | 4.40E+05 |
| 5 | 012105 | DMEM | 3 mg/ml | 3 hrs | 10 | 30 | 86.0% | 6.24E+06 | 6.24E+05 |
| 6 | 020805 | DMEM | 3 mg/ml | 3 hrs | 12.5 | 30 | 91.0% | 1.62E+06 | 1.30E+05 |
| 7 | 011305 | DMEM | 3 mg/ml | 3 hrs | 10 | 30 | 86.0% | 1.53E+05 | 1.53E+04 |
| 8 | 020505 | DMEM | 3 mg/ml | 3 hrs | 10 | 50 | 77.6% | 9.35E+06 | 9.35E+05 |
| 9 | 121804 | DMEM | 0.167 mg/ml | 3 hrs | 20 | 60 | 74.0% | 4.77E+05 | 2.39E+04 |
| 10 | 121804 | DMEM | 0.833 mg/ml | 3 hrs | 20 | 60 | 78.0% | 2.65E+06 | 1.33E+05 |
| 11 | B-031505 | DMEM | 3 mg/ml | 1 hr | 20 | 60 | n/a | 1.00E+06 | 5.00E+04 |
| 12 | 022405 | DMEM | 3 mg/ml | 3 hrs | 25 | 50 | 76.0% | 1.20E+05 | 4.80E+03 |
| 13 | 030905 | DMEM | 3 mg/ml | 3 hrs | 20 | 50 | 94.0% | 1.40E+07 | 6.99E+05 |
| 14 | 022405 | DMEM | 3 mg/ml | 3 hrs | 10 | 25 | 94.7% | 3.63E+05 | 3.63E+04 |
| 15 | 030905 | DMEM | 3 mg/ml | 24 hrs | 10 | 30 | 92.8% | 3.59E+06 | 3.59E+05 |
| 16 | 040705 | Saline | 3 mg/ml | 15 min | 10 | 30 | 66.0% | 1.30E+05 | 1.30E+04 |
| 17 | 040705 | PBS | 3 mg/ml | 10 min | 5 | 30 | 90.4% | 2.08E+05 | 4.16E+04 |
| 18 | 040705 | PBS | 3 mg/ml | 20 min | 10 | 25 | 83.0% | 1.83E+06 | 1.83E+05 |
| 19 | 040705 | PBS | 3 mg/ml | 30 min | 10 | 30 | 95.0% | 3.58E+06 | 3.58E+05 |
| 20 | 041305 | PBS | 3 mg/ml | 5 min | 15 | 30 | 92.1% | 2.05E+06 | 1.37E+05 |
| 21 | 041305 | PBS | 3 mg/ml | 10 min | 15 | 30 | 96.2% | 1.64E+06 | 1.09E+05 |
| 22 | 041305 | PBS | 3 mg/ml | 30 min | 15 | 30 | 91.9% | 3.83E+06 | 2.55E+05 |
| 23 | 041305 | PBS | 3 mg/ml | 1 hr | 15 | 30 | 90.9% | 1.78E+07 | 1.18E+06 |

The above data shows that cancellous bone treated with collagenase at various concentrations and for various periods of time in accordance with the present invention retain acceptable viability.

EXAMPLE 4

In this example, two samples of cells obtained from cancellous bone samples treated with collagenase are tested for their ability to differentiate into osteogenic cells.

A stock of a standard culture medium was prepared by pipetting 111 ml of FBS and 11 ml of antibiotic-antimycotic (Invitrogen Cat. No. 15240-062) into 1,000 ml of DMEM-low glucose (DMEM-lg) to provide a medium having a final concentration of 10% FBS and 1% antibiotic-antimycotic.

A stock of a culture medium including osteogenic supplements (OS medium) was prepared by mixing 246 ml of the standard medium with 25 $\mu$l of 1 mM dexamethasone solution, 2.5 ml of 1M $\beta$-glycerophosphate ($\beta$GP) solution, and 1.25 ml of 10 mM ascorbic acid-2-phosphate (AsAP) solution in a 500 ml sterile bottle. The materials are mixed by swirling the bottle gently for 30 seconds. The medium then is poured into the reservoir of a 500 ml 0.2.mu. filter with storage system. A vacuum line then is attached to the 500 ml 0.2.mu. filter, and the medium is filter sterilized. The reservoir then is removed and replaced with a cap. The OS medium is stored at 2.degree.-8.degree. C.

A Fast Violet B solution was prepared by placing a Sigma.®. Fast Violet B Salt Capsule into 48 ml of distilled water. The resulting solution then was aliquoted into two 50 ml conical tubes with 12 ml of solution being added to each tube. The tubes then were stored at 4.degree.C.

A citrate solution was prepared by diluting 2 ml of Sigma.®. Citrate Concentrated Solution to 100 ml with distilled water. The citrate solution was stored at 4.degree.C.

Two collagenase-treated cancellous bone samples were prepared as described in Example 1, and collagenase released (CR) cells from such samples were obtained as described in Example 2.

CR cells were plated at a density of $0.5$-$5.0 \times 10^6$ cells per well in a 6-well plate using 3 ml of the standard medium hereinabove described. The plate was labeled "PO", and covered with a lid, and transferred to a 37.degree.C. incubator set at 5% CO2 and 90%.+−.5% humidity. Medium changes were performed twice weekly with a medium volume of 3 ml per well.

Starting on day 7, the plate was examined for cell growth. Confluent cultures were trypsinized for cells between day 14 and day 21.

An appropriate volume of trypsin was warmed to 20.degree.C.-37.degree.C. in a water bath. The plate that is to be trypsinized was removed from the incubator. The medium was aspirated off, and 1.5 ml of trypsin was added to each well to be trypsinized. The plate was placed back in the 37.degree.C. incubator for 5 minutes. The plate then was removed from the incubator, and the sides and bottom of the plate were tapped to dislodge attached cells. 3 ml of standard medium then was added to the wells, the cell suspensions then were mixed, and the entire volumes from the wells were transferred into a 5.0 ml conical tube. The wells then were rinsed with 3 ml of standard medium, and the rinse medium was added to the tube. The total volume of the tube then was brought to 45 ml.

The tube then was placed in a centrifuge, and spun at 1,960 rpm for 8 minutes (about 878 g). The supernatant then was aspirated off, and the pellet was loosened gently by dragging the tube across a tube rack. The pellet then was re-suspended in an appropriate volume of standard medium (about 1 to 3 ml) for cell counting.

A 20 $\mu$l aliquot of the cell suspension then was tested for % viability and cell density as described in Example 2.

The cells then were plated at a density of $30 \times 10^3$ cells ($\pm 15 \times 10^3$ cells) per well in a 6-well plate using 3 ml standard medium. The plate then was labeled "OS", covered with a lid, and transferred to a 37.degree.C. incubator set at 5% CO.sub.2 and 90%.+−.5% humidity. The plate was incubated for 24 to 48 hours.

The OS medium was warmed to 20.degree.-37.degree.C. in a water bath. The standard medium then was aspirated off from each well of the plate, and 3 ml of OS medium then was added to each well. The OS medium was changed every third or fourth day, and the cultures were assayed for alkaline phosphatase expression between days 7 and 14.

Alkaline phosphatase staining then was conducted. Each well was rinsed twice with 1 ml of PBS. A fixative solution then was prepared by mixing two volumes of citrate working solution with three volumes of acetone. Each well then was fixed for one minute with 1 ml of the fixative solution.

0.5 ml of Sigma alkaline solution naphthol AS-MX phosphate was added to 12 ml of Fast Violet B solution. The solution then was covered with aluminum foil to protect it from light. 1 ml of the Fast Violet B/naphthol solution then was added to each well.

The plate then was incubated at room temperature, in the dark for one hour. The wells then were aspirated, and rinsed twice with 1 ml of distilled water. Cell cultures that exhibited a distinct pink stain in some or all of the cells were positive. Cell cultures from both samples of cells gave positive results.

The disclosures of all patents, publications (including published patent applications), depository accession numbers, and database accession numbers were incorporated herein by reference to the same extent that each patent, publication, depository accession number and database accession number were specifically and individually incorporated by reference.

It is to be understood, however, that the scope of the present invention is not to be limited to the specific embodiments described above. The invention may be practiced other than as particularly described and still be within the scope of the accompanying claims.

What is claimed is:

1. A bone implant comprising:
cancellous bone comprising a bone matrix and viable osteogenic cells native to the cancellous bone and contained within the bone matrix, and wherein the cancellous bone is essentially free of blood cells, wherein the bone implant is configured to be injected directly at an implantation site.

2. The bone implant of claim 1 further comprising demineralized bone.

3. The bone implant of claim 2, wherein each of the cancellous bone and demineralized bone are 50% in volume of the bone implant.

4. The bone implant of claim 1, wherein the cancellous bone is processed so that at least part of a cortical shell thereof is removed, and wherein the cancellous bone is cut or milled into desired sizes or shapes.

5. The bone implant of claim 1, wherein the cancellous bone is treated with one or more antibiotics or one or more antimycotics.

6. The bone implant of claim 1 further comprising a cryopreservative or vitrification medium.

7. The bone implant of claim 6, wherein the bone implant is frozen and then thawed prior to the injection.

8. The bone implant of claim 7, when frozen, is stored at −80 degrees Celsius ±5 Celsius for a period of at least seventeen days.

9. The bone implant of claim 8, wherein upon thawing of the bone product, at least 70% of the viable osteogenic cells are still viable.

10. The bone implant of claim 8, wherein upon thawing of the bone product, density of the viable osteogenic cells native to the cancellous bone is at least $1\times10^3$ cells/cc.

11. The bone implant of claim 1, wherein at least a part of the bone implant is configured to be retained at an implantation site long enough for initialization of bone formation.

12. A bone implant comprising:
cancellous bone comprising a bone matrix and viable osteogenic cells native to the cancellous bone and contained within the bone matrix, the cancellous bone being essentially free of blood cells; and
demineralized bone,
wherein at least a part of the bone implant is configured to be retained at an implantation site long enough for initialization of bone formation.

13. The bone implant of claim 12, wherein each of the cancellous bone and demineralized bone are 50% in volume of the bone implant.

14. The bone implant of claim 12, wherein the cancellous bone is processed so that at least part of a cortical shell thereof is removed, and wherein the cancellous bone is cut or milled into desired sizes or shapes.

15. The bone implant of claim 12, wherein the cancellous bone is treated with one or more antibiotics or one or more antimycotics.

16. The bone implant of claim 12 further comprising a cryopreservative or vitrification medium.

17. The bone implant of claim 16, wherein the bone implant is frozen and then thawed prior to a use.

18. The bone implant of claim 17, when frozen, is stored at −80 degrees Celsius ±5 Celsius for a period of at least seventeen days.

19. The bone implant of claim 18, wherein, upon thawing of the bone product, at least 70% of the viable osteogenic cells are still viable, and density of the viable osteogenic cells native to the cancellous bone is at least $1\times10^3$ cells/cc.

* * * * *